United States Patent [19]
Benner et al.

[11] Patent Number: 5,935,519
[45] Date of Patent: Aug. 10, 1999

[54] APPARATUS FOR THE DETECTION OF SULFUR

[75] Inventors: Richard L. Benner, Fairbanks, Ak.; Donald H. Stedman, Denver, Colo.

[73] Assignee: Sievers Instruments, Inc., Boulder, Colo.

[21] Appl. No.: 08/862,485

[22] Filed: May 23, 1997

Related U.S. Application Data

[63] Continuation of application No. 08/441,829, May 16, 1995, Pat. No. 5,661,036, which is a continuation of application No. 07/873,402, Apr. 24, 1992, Pat. No. 5,424,217, which is a continuation of application No. 07/275,980, Nov. 25, 1988, abandoned.

[51] Int. Cl.$^6$ .................................................. G01N 25/22
[52] U.S. Cl. ........................... 422/52; 436/119; 436/121; 436/155; 436/172
[58] Field of Search .................................. 436/120, 119, 436/121, 155, 172; 422/52, 83, 85, 86

[56] References Cited

U.S. PATENT DOCUMENTS

| | | | |
|---|---|---|---|
| 4,066,409 | 1/1978 | Fine | 436/123 |
| 4,190,368 | 2/1980 | Etess | 422/52 |
| 4,352,779 | 10/1982 | Parks | 436/123 |
| 4,678,756 | 7/1987 | Parks | 436/123 |
| 4,717,675 | 1/1988 | Sievers | 436/103 |
| 5,614,417 | 3/1997 | Kubala | 436/120 |

OTHER PUBLICATIONS

Shearer et al., "Analysis of sulfur compounds by capillary column gas chromatography with sulfur chemiluminescence detection", *J. of Chromat. Science*, vol. 28, pp. 24–28 (Jan. 1990).

*Primary Examiner*—Lyle A. Alexander
*Attorney, Agent, or Firm*—Lappin & Kusmer LLP

[57] ABSTRACT

A process and apparatus are disclosed for the detection and measurement of sulfur in both organic and inorganic sulfur-containing compounds. The process includes admixing a sample including a sulfur-containing compound with oxygen, and then exposing the mixture to a source of combustion causing heat in the presence of a combustion supporting reducing agent at a combustion site. The resulting gaseous combustion products are vacuum extracted from the combustion site, and then directed into a darkened low pressure chamber. The combustion products in the low pressure chamber are then contacted with ozone, with the result that the sulfur combustion products are converted to chemiluminescent sulfur dioxide. The emitted chemiluminescence is then detected, and may be measured to provide a quantitative indication of the amount of sulfur in the original sample. The preferred source of oxygen is air, the preferred form of combustion heat is a flame, and the preferred form of reducing agent is hydrogen gas.

23 Claims, 2 Drawing Sheets

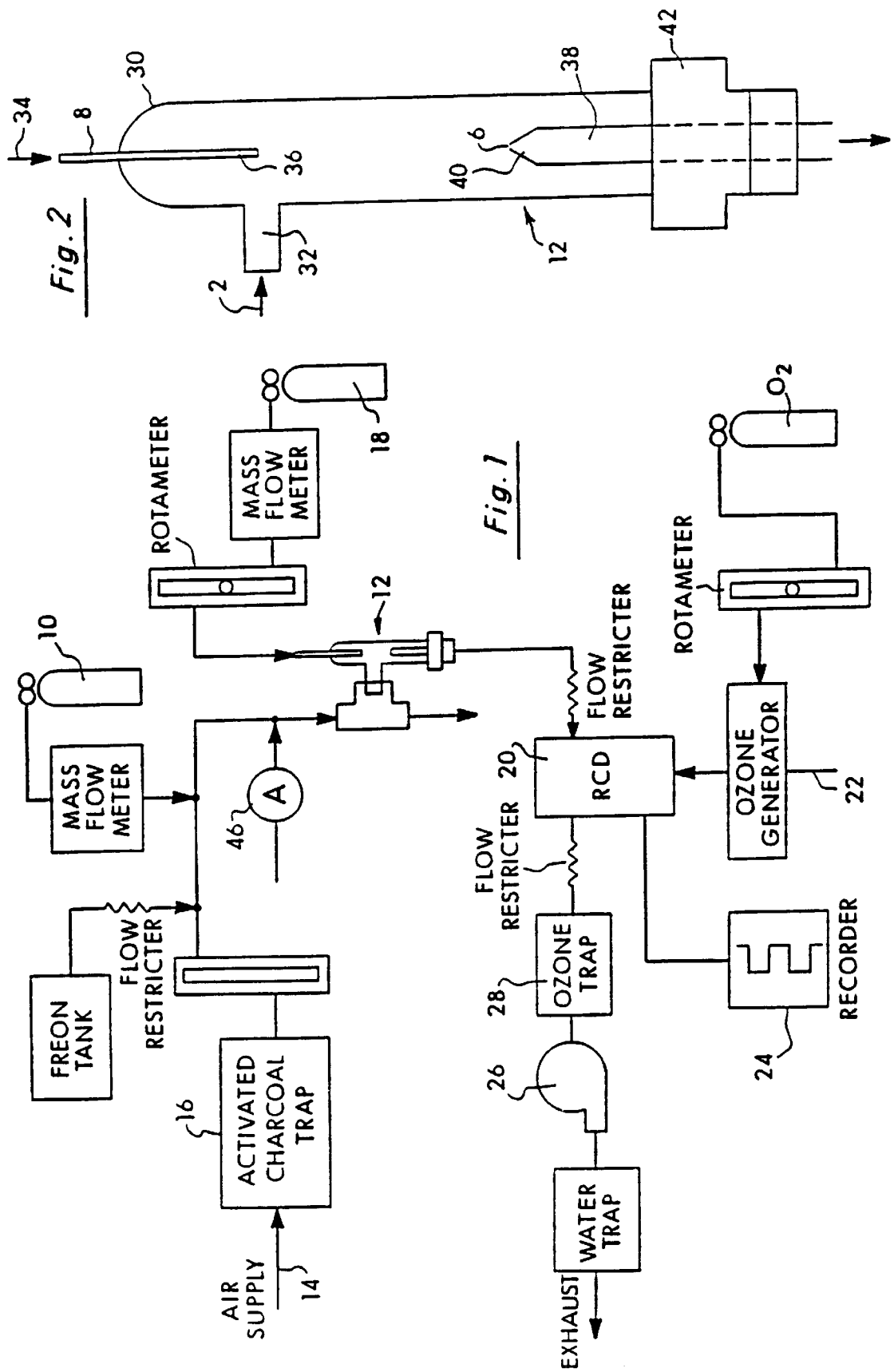

APPARATUS FOR THE DETECTION OF SULFUR

CROSS-REFERENCE TO RELATED APPLICATIONS

This application is a continuation of Ser. No. 08/441,829, filed May 16, 1995, now U.S. Pat. No. 5,661,036 issued Aug. 26, 1997; which was a continuation of Ser. No. 07/873,402, filed Apr. 24, 1992, now U.S. Pat. No. 5,424,217 issued Jun. 13, 1995; which in turn was a continuation of Ser. No. 07/275,980, filed Nov. 25, 1988, now abandoned.

BACKGROUND OF THE INVENTION a) Field of the Invention

The present invention relates generally to processes and apparatus for detection and measuring of chemically-bound sulfur, and more particularly, to the detection and measurement of sulfur combustion products which have been contacted by ozone to form chemiluminescent reaction products. The present invention also relates to improved processes and apparatus for enhancing the chemiluminescent detection of sulfur by the reduction of interfering compositions.

b) Discussion of the Prior Art

Numerous processes and apparatus have been devised for detecting and measuring chemical substances. Among detectors used to detect and measure fluids, whether from an independent source, or from the output of a gas chromatographic apparatus, are those using thermal conductivity, hydrogen flame ionization, electronic capture, alkaline flame ionization, and flame photometry. Of particular interest in recent years has been the sensitive and selected detection of sulfur compounds, both as a pollutant in the environment, and from other sources. The most widely utilized sulfur selective detector at the present time is the flame photometric detector (FPD). The FPD device and process is based on the fact that a hydrogen flame in the presence of air (oxygen) emits electromagnetic radiation, usually in the form of visible spectra light. In practice, a carrier fluid transporting a to-be-tested substance, for example an eluent separated from a sample by a chromatographic instrument, is mixed with an air stream (which may be oxygen enriched), and passed into a hydrogen burner, or a burner in the presence of hydrogen. The resulting mixture contains hydrogen in excess of that required for complete combustion of the oxygen present. The luminous radiation caused by this combustion impinges or is reflected through an optical filter which has been selected according to the desired radiation wavelength of the substance to be measured. Subsequently, the light from the filter passes to a light detector, such as a photomultiplier tube. The photomultiplier tube produces a current which can be detected, measured, analyzed, recorded, and so on, to indicate the substance and the amount of the substance. Such an FPD system can be used as a specific selective detector and process for sulfur in sulfur-containing substances since a specific wavelength is emitted from the formation of the molecular species of sulfur during the burning of the hydrogen flame. Such an FPD system is relatively sensitive and has been widely used, for example in pollution control and determination. However, the fundamental response of such FPD detectors to sulfur is not linear with respect to the concentration of the to be measured sulfur, and are difficult to calibrate with accuracy, especially for the measurement of low concentrations of sulfur. Another distinct problem with FPD devices is that numerous other components in the sample can interfere with accurate determination of sulfur.

Another approach to measuring sulfur-containing compounds in a fluid sample includes the use of chemiluminescence detection schemes.

There remains a need for a process and device capable of measuring sulfur compounds accurately, quickly and in the low femtogram range without being sensitive to interference of other compounds and components of the sample being tested.

SUMMARY OF THE INVENTION

In view of the foregoing, it is an object of the present invention to provide a process and device for detecting and measuring sulfur in a fluid sample, and in particular in an environmental air sample or a chromatographic eluent.

It is another object of the present invention to provide a process and device for detecting sulfur-containing compounds in a rapid and continuous manner without regard to the presence of other compounds in the sample.

A further object of the present invention is to provide a novel and improved method and apparatus for measurement of sulfur-containing compounds by chemiluminescent reaction with ozone at low pressures in such a way as to be sensitive to sulfur compounds, but insensitive to water vapor, carbon dioxide or other hydrocarbon interferences.

Accordingly, the present invention discloses and teaches a process and apparatus for the detection and measurement of bound sulfur in organic and inorganic sulfur containing compounds. The process includes admixing a fluid sample having a sulfur-containing compound with an oxygen source. This mixture is then exposed to a combustion causing heat source, such as a flame, in the presence of a reducing agent. The resulting gaseous combustion products are then vacuum extracted from the combustion site, and then directed into a darkened low pressure chamber. The combustion products in the low pressure chamber are then contacted with ozone, with the result that the sulfur combustion products are converted to chemiluminescent sulfur dioxide in an excited state. Finally, the chemiluminescence is detected and measured to provide an indication of the amount of sulfur in the fluid sample. The preferred source of oxygen is air, the preferred form of combustion heat is a flame, and the preferred form of reducing agent is hydrogen gas.

In one particular preferred embodiment of the invention, a halogenated compound is injected into the sample mixture prior to or at the time that it is subjected to combustion.

As described in greater detail below, the present invention utilizes a hydrogen-air flame to produce a combustion product of either sulfur monoxide (SO) or hydrogen sulfide ($H_2S$) for subsequent reaction with ozone. It should be noted that, because of its thermal instability, ozone cannot be directly introduced at the combustion site as a feasible means of exploiting the chemiluminescent reaction of ozone with the combustion products. Various studies have shown that a significant portion of sulfur entering a flame produces sulfur monoxide. In fact, the sulfur monoxide so produced is present in the flame combustion products in concentrations which are about ten times greater than atomic sulfur, which is the substance which is normally measured by conventional FPD processes and apparatus. However, it is a possibility that the process of the present invention actually produces $H_2S$, and then detects the chemiluminescent reaction of $H_2S$ with ozone. Nevertheless, it is believed that the principal combustion product is sulfur monoxide. Regardless of whether SO or $H_2S$ is produced as the combustion product, they both produce approximately the same wavelength of light during the chemiluminescent reaction with ozone.

The present invention utilizes a narrow capillary sampling probe, discussed below, which is designed to quickly draw substantially all of the combustion products to a low temperature and low pressure chamber for reaction with ozone. An important and preferred aspect of the present invention is that by lowering the pressure of the combustion product gases to a pressure within the range of about of 1 torr to about 50 torr, with approximately 10 torr preferred, the chemical combustion reactions are quenched, the possibility of condensation of water produced during combustion is eliminated, and the gas mixture of combustion products can be rapidly transferred to a light tight chamber for contact and chemical reaction with ozone. These and other objects of the present invention will become apparent to those skilled in the art from the following detailed description, showing the contemplated novel construction, combination, and elements as herein described, and more particularly defined by the appended claims, it being understood that changes in the precise embodiments of the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 1 is a schematic diagram of the apparatus of the present invention embodying the process of the present invention;

FIG. 2 is a schematic diagram of an adjustable combustion assembly utilized in the present invention.

DESCRIPTION OF THE PREFERRED EMBODIMENT

Figure 3:
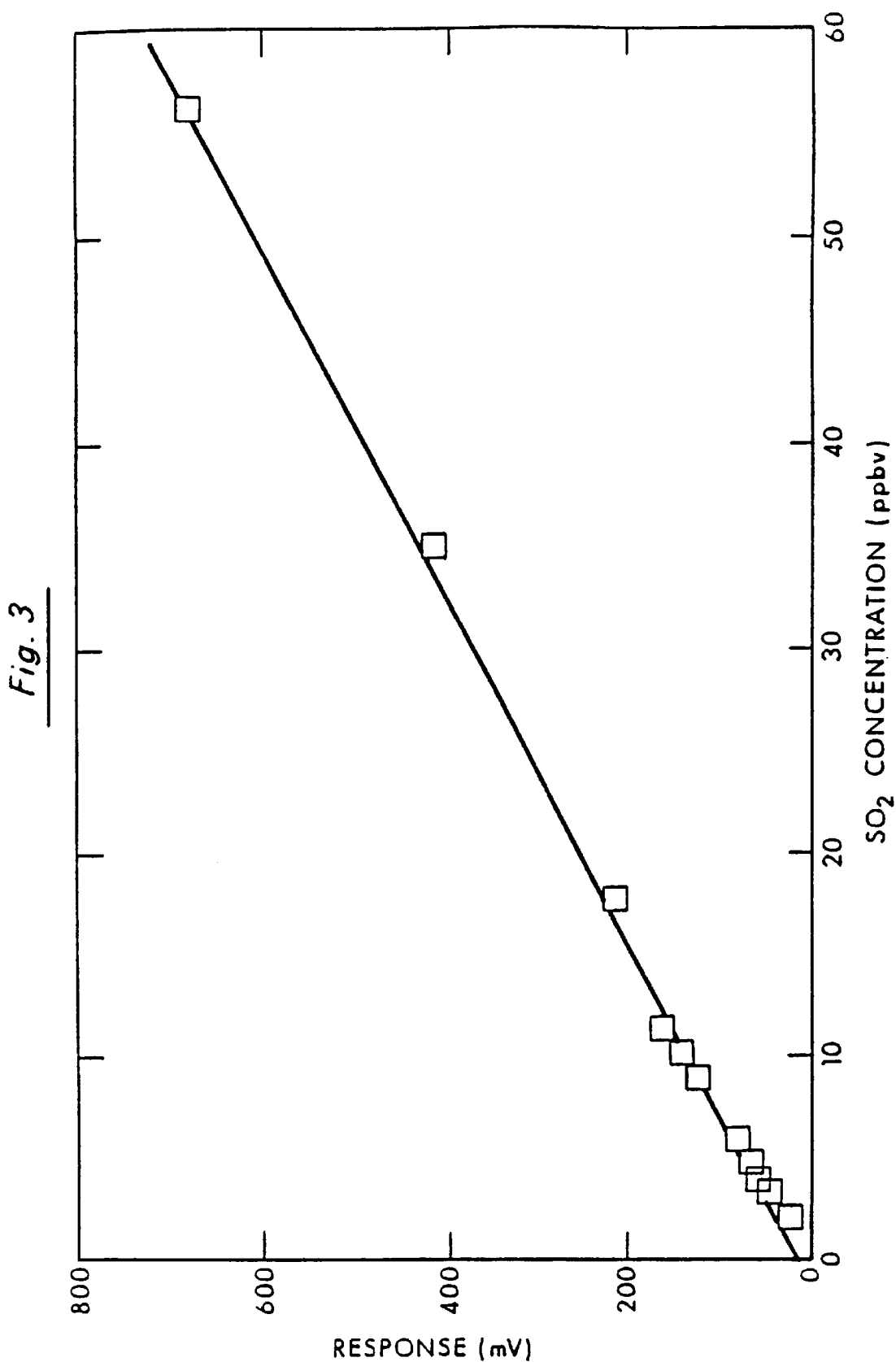
FIG. 3 is a graph illustrating sulfur dioxide concentration in parts per billion based on photomultiplier tube measurements of chemiluminescent light produced from samples measured using the process and apparatus of the present invention.

Referring now to FIG. 1, a schematic diagram of the present version of the apparatus is illustrated therein. Referring first to a general overview of the process of the invention, a fluid sample (either gas or liquid) which contains a sulfur compound, from a source 10 is directed to a combustion site, in this case burner assembly 12. The to-be-tested sample is admixed with oxygen from a source 14 prior to reaching the combustion assembly 12. In preferred practice, oxygen is derived from an ambient air supply and is scrubbed through an activated charcoal trap 16 to remove ambient sulfur prior to admixture with the sulfur sample from 10. The sulfur/oxygen sample is then exposed to combustion causing heat in flame assembly 12 in the presence of a reducing agent from a source 18. The reducing agent is preferably hydrogen. The gaseous combustion products of the flame from the assembly 12 are immediately vacuum extracted through a flow restricted orifice to a darkened, low pressure, ambiant temperature reaction chamber 20. Ozone is continuously directed into reaction chamber 20 from an ozone generator or other ozone source 22. In reaction chamber 20 ozone is admixed and reacted with the gaseous combustion products from combustion assembly 12. This particular procedure results in the production of chemiluminescent radiation from excited $SO_2$ which radiation is measured by a light detector, such as a photomultiplier tube, and recorder assembly combination 24. The low pressure in the chamber 20 and at the orifice of the assembly 12 is maintained by a vacuum pump 26 which also assists in removing the products from the reaction chamber 20 after chemiluminescence.

In experimental form, the sulfur-containing sample from source 10 was a calibrated sulfur gas of known concentration. While any reducing agent may be utilized, hydrogen is preferred. While hydrogen is the preferred reducing agent, other reducing agents such as methane, butane, propane, alcohols, aldehydes, amines, ketones, olefins, and aromatic compounds may be used in the practice of the present invention.

Many of the details of reaction chamber 20 are described in greater detail in Sievers et al. U.S. Pat. No. 4,717,675. One of the differences between reaction chamber 20 of the present invention and the RCD disclosed in the referenced patent is that the measurement of sulfur dioxide chemiluminescence produced by the present invention requires a blue sensitive photomultiplier tube. The present system includes an ozone trap 28 to prevent ozone from inadvertently entering the atmosphere or the vacuum pump. Any desired or standard ozone generator 22 may be utilized in the present invention.

In one embodiment of the present invention, a Radox Chemiluminescence Detector model 270, from Sievers Research, Boulder, Colo. was obtained and then modified according to the present invention. Modifications to this commercially available unit included the replacement of the standard photomultiplier tube with a blue sensitive one (model R 268 Hamamatsu) as indicated previously, replacement of the glass window with a fused quartz window, and the addition of an optical filter (7–54 Coming Glass Works, Coming, N.Y.). The optical filter transmits between about 240 and about 410 nanometers with a peak transmittance of about 82% at 320 nm. In addition, the reaction cell was modified to accommodate greater sample flow rates. Larger flow rates were achieved by replacement of the standard 25 liter/minute vacuum pump with a 300 liter/minute model (Model 1012, Alcatel, France). A high capacity ozone generator was utilized which could produce nearly ten times more ozone, 100 $cm^3$/minute, than the ozone generator in the standard RCD reaction chamber. Dilution air used in the dynamic dilution calibration system was metered by a rotometer and calibration standards of sulfur gases as well as hydrogen were metered with mass flow meters.

Dilution air for the ambient air supply 14 was obtained from the laboratory bench, but first passed through the activated charcoal absorbent bed 16 as previously indicated. All tubing between the sample orifice and the reaction chamber reaction cell was coated with halocarbon wax (Series 1200, Halocarbon Products, Hackensack, N.J.) to minimize loss of the SO to wall reactions. Oxygen supplied to the ozone generator and hydrogen were standard grade and no provisions were made to remove contaminants from the gases. The sample orifice was empirically sized to provide a total flow of 500 actual $cm^3$/min in a reaction cell pressure of 9–10 torr, as discussed below.

FIG. 2 illustrates a preferred arrangement for burner assembly 12. More specifically, assembly 12 is of quartz and is built to contain a combustion heat source in the form of a diffusion flame. The assembly 12 includes a quartz housing 30 with a sample/air intake vent 32. Hydrogen or another reducing agent is injected through an injection vent 34 which projects into the housing 30. The terminal end 36 of the vent tube 34 is the site of the diffusion flame. A quartz probe 38 terminating in an orifice 40 projects within the housing 30. The flame resides between the terminal end of the probe 38 and the end 36 of the tube 34. The probe 38 mounted to a sliding seal 42, permits the distance between the end of the probe 38 and the end 36 of tube 34 to be varied. In this manner, the residence time of the sample in the burner may be varied from 1–40 ms. In preferred form, the residence time of the sample in the burner is 4 ms/cm. In alternate form, the flame from an FID (flame ionization detector) may also be used as a flame source for the present invention. Moreover, any type of flame source may be utilized to react the sample with oxygen and reducing agents to generate the product gases for subsequent reaction with ozone and chemiluminescence from excited sulfur dioxide.

Preliminary testing of the present invention for sulfur uses the detector in a real-time analysis mode. It is found to be important that the post-flame pneumatic system be maintained at as low a pressure as possible for a variety of reasons. First, the intensity of the chemiluminescent reaction was found to be inversely proportional to pressure with a half-quenching pressure of about 0.02 torr. In addition, the gaseous sample stream produced from the flame is about 25% water vapor requiring that the pneumatic system be maintained well below the vapor pressure of water (about 50 torr) to prevent condensation. Such condensation would dramatically interfere with the chemiluminescent aspects of the invention. Also, the post-flame reactions are effectively quenched at low pressure allowing the SO radical to be transported to the reaction chamber. All data presented below are based on a sample air flow of 500 $cm^3$/min, a cell pressure of 50 torr, and 6% $O_3$ in 100 $cm^3$ in 100 $cm^3$ of $O_2$. The addition of the UV filter in the reaction chamber decreased a high baseline signal to less than 0.5% of full scale. Typical parameters for the example shown below include 300 ml/min of hydrocarbon reducing agent, 500 ml/min of air and sample into the flame, and a system pressure of approximately 10 torr in addition to an oxygen flow of approximately 100 ml/min.

Equivalence ratio is defined as the ratio of the actual hydrogen flow rate to the hydrogen flow rate needed for stoichiometric combustion. From test results utilized in the process of the present invention, the sensitivity of the present invention to sulfur dioxide and all other sulfur containing gases tested is a function of the equivalence ratio. It was found that the optimal equivalence ratio is between 1.4–1.6. This optimum equivalence ratio is independent of the sample residence time in the flame, and thus the sample orifice position. It is believed that the reason for the sharp optimum equivalence ratio is because there must be sufficient hydrogen to react with molecular oxygen thus reducing the rate at which SO is converted to $SO_2$, without reducing the flame temperature to the point that SO is not formed.

With respect to the flame residence time, it was determined that the optimum flame residence time is approximately 2.5 ms. The sensitivity as a function of the flame residence time decreases very rapidly at shorter flame residence times probably because the combustion is incomplete and SO (or $H_2S$) is not formed. At longer residence times, the signal reaches a constant value at the SO equilibrium concentration, but the background noise increases due to a less stable flame.

With respect to the effect of ozone flow and concentration, a standard reaction chamber ozone generator was initially used. The ozone concentration produced with oxygen is twice that produced using dry air, and a corresponding improvement in sensitivity was observed. As a result, the apparatus of the present invention was switched to the larger ozone generator thereby increasing ozone concentration by ten times. This showed an increase in sensitivity by a factor of 2. The ozone flow rate at which the sensitivity is optimum corresponds to 6 ml ozone per minute in 100 $cm^3$/min of oxygen. The flame produced a large amount of NO which also reacts with ozone thus requiring an unusually large amount of ozone. However, the NO reaction did not in any way interfere with the chemiluminescence of sulfur dioxide and the measurement thereof, because it occurs at a longer wavelength not passed by the optical filter.

Two common interfering species for the previous flame photometric detector processes and apparatus operated in real time mode are carbon dioxide and water vapor.

The process and device of the present invention demonstrated no effect on either the baseline signal or the response to a given concentration of $SO_2$ for water vapor between 0.4% and 3.0%, which is equivalent of 12–83% relative humidity at 23° C. It also demonstrated no effect of carbon dioxide concentration between 350 ppmv and 1700 ppmv. In chromatographic analyses, two compounds which commonly coelute are methylethyl sulfide (MES) and hexane. The hexane enhances the sulfur signal at low sulfur concentration and quenches the sulfur signal at high sulfur concentration. Tests utilizing the present invention for various flame residence times demonstrated that it is possible to eliminate any interference from hexane entirely by adjusting the flame residence time. In another test, the response to sulfur dioxide as a function of heptene concentration at a fixed flame residence time of 7.5 ms was studied. Heptene causes a large signal in other sulfur monitors. The heptene was responsible for an enhancement of the $SO_2$ signal. The present invention did not have any detectable response to clean air, that is with no sulfur, with concentrations of either hexane or heptene up to 4000 ppmv. Apparently, the flame chemistry is perturbed by the hydrocarbon in such a way that SO production is affected to a minor extent. It should be pointed out that the effect of the present invention's response from hydrocarbons is $10^4$–$10^5$ less than that reported for FPD devices presently utilized.

EXAMPLE I

The process and system illustrated in FIG. 1 and discussed above was used intermittently for approximately 30 days. The standard parameters discussed above were applied. During this time, the baseline signal was very stable and good sensitivity to sulfur dioxide was obtained. The results of these tests are illustrated in FIG. 3 showing a consistent and good sensitivity to sulfur dioxide concentration.

EXAMPLE II

It was observed that after nearly two months of working with the process and device of the present invention as described in EXAMPLE I, the baseline signal would start to increase continuously. In spite of the increase in baseline, it was determined without question that the process and apparatus of the present invention had a sensitive response to each of the sulfur compounds tested, that is methyl ethyl sulfide, ethyl mercaptan, dimethyl sulfide, sulfur dioxide, sulfur hexafluoride and hydrogen sulfide. However, with the increase in baseline quantification of the response became impossible. This background chemiluminescence increased when the ozone generator was turned off so that only oxygen was reacting with sample gases and disappeared completely when the oxygen flow was stopped. The absolute intensity of the background signal was not sufficiently intense to allow spectral analysis. Consequently, the results were that the chemiluminescence continued even after the flow of sulfur compounds was stopped.

The following observations were made when the baseline was too high and irregular to allow analytical use of the process and device of the present invention:

1) The baseline signal increased when the power to the ozone generator was turned off.

2) The baseline signal decreased to zero if the oxygen flow was stopped completely.

3) The sensitivity to sulfur dioxide decreased if the baseline was high compared to the sensitivity when the baseline was at its normal low level.

4) The magnitude of the baseline signal was affected by changing the hydrogen flow rate. The highest baseline signal was observed with the same hydrogen flow rate that produced the most sensitive response to sulfur.

5) The baseline signal could be decreased for a period of time to a very low and acceptable value by momentary injection of any halogenated compound into the flame.

6) Replacement of the quartz sample orifice with a newly fabricated one did not affect the baseline signal.

Since it was found that the addition of a small amount of a halogenated compound to the flame would eliminate the baseline drift without affecting the sensitivity to sulfur, it is theorized that the reactive species responsible for the background luminescence is scavenged by the halogens. The chemical species which produces the chemiluminescence with oxygen in the flame is unknown. Consequently, in order to maintain a low baseline over a long period of use of the process and apparatus of the present invention, one embodiment of the present invention introduces a halogenated compound, such as fluorocarbon 12, fluorocarbon 11, or carbon tetrachloride to the sample at point 46 illustrated in FIG. 1, introducing the halogenated compounds into the oxygen and sample at or immediately before the flame, or in the hydrogen flow. With the addition of fluorocarbon or other halogenated compound, the baseline has been observed to be low and stable. The observed change was from a maximum to a minimum the equivalent of less than 0.2 ppbv sulfur during 75 hours of continuous observation.

EXAMPLE III

In an attempt to remedy the problem outlined in EXAMPLE II above, several different materials were used as the flow system walls in the belief that one would react with and thus remove the species causing the high baseline signal. All six materials tested provided a short period of acceptable baseline signal. The materials and times tested are listed below in TABLE I.

| MATERIALS | TIME |
| --- | --- |
| halocarbon wax | 18 hours |
| halocarbon oil | 7 hours |
| paraffin wax | 10 hours |
| aluminum (type 6061-t6) | 3 hours |
| stainless steel (type 304) | 6 hours |
| Teflon | 0 hours |

When it became apparent that the switching of flow system materials would provide only temporary reductions in baseline, a new approach was pursued.

EXAMPLE IV

The new approach discussed in EXAMPLE III and discussed also in part above, involved the addition of a halogenated compound on a continuous basis. A continuous flow of 0.45 cm$^3$/min of $CF_2Cl_2$ was introduced into the sample air producing a concentration of hundreds of ppm. The baseline was observed to be stable for indefinite periods with the chlorofluorocarbon addition. Two other chlorofluorocarbon concentrations have been used, 40 and 180 ppmv, and both work equally well for the reduction of the baseline. In addition, neither of the two chlorofluorocarbon concentrations affected, either positively or negatively, the sensitivity of the process and apparatus of the present invention to sulfur compounds. With the addition of 40 ppm chlorofluorocarbon, it was possible to quantify the response to different sulfur compounds. These results indicated that the sensitivity to the sulfur compounds listed above in EXAMPLE II as well as $H_2S$ are all equal. It should be emphasized that the chlorofluorocarbon could be added to the flame, either into the air stream or into the hydrogen flow with the same result.

EXAMPLE V

The present invention has a variety of system applications. Reconfiguration of the system in only minor details provides different uses for the device and process of the invention. In this example, the addition of a chromatographic effluent into point A, that is 46 of FIG. 1, provides species specific detection of sulfur and removal of the activated charcoal trap (16) provide a means of monitoring concentrations of total sulfur in ambient air.

The process and apparatus of the present invention for the detection and monitoring of sulfur has been shown to be a very sensitive, selective and linear detector operated in the real-time mode. The present invention provides detection limits at similar levels reported for flame photometric detectors but at response times which are at least 30 times faster. The present invention does not suffer from the interference problems experienced by the flame photometric detectors of the prior art from water vapor or carbon dioxide and four to five orders of magnitude less for hydrocarbons. The present invention also provides uniform response to different sulfur compounds which greatly enhances its utility as a gas chromatographic detector. Finally, the present invention provides much more accurate and faster sulfur detection capability than either flame photometric detectors known previously hereto or prior detection devices which are based on chemiluminescence of reaction of ozone with the air sample directly.

It will be understood that the invention may be embodied in other specific forms without departing from the spirit or central characteristics thereof. The present examples and embodiments, therefore, are to be considered in all respects as illustrative and not specifically restrictive, and the invention is not to be limited to the details given herein but may be modified within the scope of the appended claims as limited by the prior art.

What is claimed is:

1. A system for detection and measurement of sulfur consisting essentially of:

(a) at least one first site for exposing a sulfur-containing compound to such conditions that a gaseous product is produced, said gaseous product including at least a chemical species which reacts with a gas containing at least ozone and oxygen to produce radiation in a range in which electronically excited sulfur dioxide produces radiation;

(b) extraction means for removing from said first site at below-atmospheric pressure at least a portion of said gaseous product;

(c) conduit means for conveying at below-atmospheric pressure said portion of said gaseous product directly from said at least one first site to a second site;

(d) gas introduction means for introducing to said second site a gas containing at least ozone and oxygen to mix with said portion of said gaseous product;

(e) pressure-reducing means for establishing below-atmospheric pressure at said second site, in said conduit means, and in said extraction means; and, (f) radiation detection and measuring means associated with said second site to detect and measure radiation from said second site in a range in which electronically excited sulfur dioxide produces radiation.

2. A system according to claim 1 wherein said pressure-reducing means comprises means to establish pressures at said second site, in said conduit means, and in said extraction means low enough to prevent condensation of water from said portion of said gaseous product.

3. A system according to claim 1 wherein said pressure-reducing means comprises means to establish pressures at said second site, in said conduit means, and in said extraction means of less than about 50 torr.

4. A system according to claim 3 wherein said pressure-reducing means comprises means to establish pressures of about 1 to 50 torr.

5. A system according to claim 1 wherein said radiation detection and measuring means detects and measures radiation substantially exclusively in the range in which electronically excited sulfur dioxide produces radiation.

6. A system according to claim 1 wherein said radiation detection and measuring means detects and measures radiation substantially exclusively in the range of about 240 to 410 nanometers.

7. A system according to claim 1 wherein a first site is connected to a source of a gas containing at least molecular oxygen and to a source of a gas containing at least molecular hydrogen.

8. A system according to claim 1 wherein said gas introduction means comprises means for producing ozone gas from a gas containing at least oxygen.

9. A system for detection and measurement of sulfur consisting essentially of:

(a) at least one first site for reacting a sulfur-containing compound in the presence of molecular oxygen and a reducing agent to produce a reaction product including at least one chemical species which reacts with a gas containing at least molecular oxygen and molecular ozone to produce radiation in the range of about 240 to 410 nanometers;

(b) means for conveying at least a portion of said reaction product at a pressure less than atmospheric pressure to a second site;

(c) means for maintaining said second site at a pressure less than atmospheric pressure;

(d) means for introducing to said second site a gas containing at least molecular oxygen and molecular ozone to mix with said portion of said reaction product;

(e) means for detecting and measuring radiation from said second site in the range of about 240 to 410 nanometers.

10. A system according to claim 9 wherein said means for maintaining said second site at a pressure less than atmospheric pressure comprises means for maintaining said second site at a pressure of about 1 to 50 torr.

11. A system according to claim 9 wherein said means for detecting and measuring radiation from said second site comprises means for measuring radiation substantially exclusively in the range of about 240 to 410 nanometers.

12. A system according to claim 9 wherein a first site is connected to a source of a gas containing at least molecular oxygen and to a source of a gas containing at least molecular hydrogen.

13. A system according to claim 9 wherein said means for introducing to said second site a gas containing at least molecular oxygen and molecular ozone comprises means for producing molecular ozone from a gas containing at least molecular oxygen.

14. An apparatus for detecting and measuring sulfur in a sample containing at least a sulfur-containing compound, said apparatus consisting essentially of:

(a) a mixing site for forming a mixture of said sample and a gas containing at least molecular oxygen, and fluid connections between said mixing site and both a sample source and a source of said gas for simultaneously feeding said sample and said gas to said mixing site;

(b) a combustion site located downstream from said mixing site for combusting at least a portion of said mixture of said sample and said gas in the presence of a reducing agent to form a combustion product, and fluid connections between said combustion site and both said mixing site and a source of a gaseous reducing agent;

(c) a chemiluminescence site located downstream from said combustion site for mixing at least a portion of said combustion product with ozone to produce chemiluminescence, and fluid connections between said chemiluminescence site and both said combustion site and a source of ozone;

(d) pressure-reducing means for establishing below-atmospheric pressure at said chemiluminescence site and in the fluid connection between said chemiluminescence site and said combustion site; and, (e) a chemiluminescence detector in association with said chemiluminescence site to detect and measure chemiluminescence produced at said chemiluminescence site.

15. An apparatus according to claim 14 further wherein said fluid connection between said chemiluminescence site and said combustion site includes a fluid flow restrictor.

16. An apparatus according to claim 14 wherein said pressure-reducing means comprises means to establish pressures at said chemiluminescence site and in said fluid connection between said chemiluminescence site and said combustion site low enough to prevent condensation of water from said portion of said gaseous product.

17. An apparatus according to claim 16 wherein said pressure-reducing means comprises means to establish pressures of less than about 50 torr.

18. An apparatus according to claim 16 wherein said pressure-reducing means comprises means to establish pressures of about 1–50 torr.

19. An apparatus according to claim 14 wherein said pressure-reducing means comprises means to establish pressures at said chemiluminescence site and in said fluid connection between said chemiluminescence site and said combustion site low enough to effectively quench chemical combustion reactions in the combustion product.

20. An apparatus according to claim 19 wherein said pressure-reducing means comprises means to establish pressures of about 10 torr.

21. An apparatus according to claim 14 wherein said chemiluminescence detector measures radiation substantially exclusively in the range in which electronically excited sulfur dioxide produces radiation.

22. An apparatus according to claim 14 wherein said chemiluminescence detector detects and measures radiation substantially exclusively in the range of about 240 to 410 nanometers.

23. Apparatus for detecting and measuring sulfur in a sample containing at least a sulfur-containing compound, said apparatus consisting essentially of:
(a) a mixing site for forming a mixture of said sample and a fluid containing at least a reducing agent and fluid connections between said mixing site, a source of said sample and a source of said fluid for simultaneously feeding said sample and said fluid to said mixing site;
(b) a reaction site located downstream from said mixing site for reacting at least a portion of said mixture of said sample and said fluid in the presence of a gas containing at least molecular oxygen at high temperature to form a reaction product, and fluid connections between said reaction site and both said mixing site and a source of said gas;
(c) a chemiluminescence site located downstream from said reaction site for mixing at least portion of said reaction product with at least ozone to provide chemiluminescence, and fluid connections between said chemiluminescence site and both said reaction site and a source of said ozone;
(d) pressure-reducing means for establishing below-atmospheric pressure at said chemiluminescence site and in the fluid connection between said chemiluminescence site and said reaction site; and
(e) a chemiluminescence detector in association with said chemiluminescence site to detect and measure chemiluminescence produced at said chemiluminescence site in the range in which electronically excited sulfur dioxide produces radiation.

\* \* \* \* \*